US00PP31227P2

(12) United States Plant Patent
Walters et al.

(10) Patent No.: US PP31,227 P2
(45) Date of Patent: Dec. 10, 2019

(54) ***SEDUM* PLANT NAMED 'DREAM DAZZLER'**

(50) Latin Name: ***Sedum* hybrid**
Varietal Denomination: Dream Dazzler

(71) Applicant: Christopher M. Hansen, Zeeland, MI (US)

(72) Inventors: Logan Walters, Hudsonville, MI (US); Christopher M. Hansen, Zeeland, MI (US)

(73) Assignee: Christopher M. Hanson, Zeeland, MI (US)

( * ) Notice: Subject to any disclaimer, the term of this patent is extended or adjusted under 35 U.S.C. 154(b) by 0 days.

(21) Appl. No.: 15/998,142

(22) Filed: Jul. 9, 2018

(51) Int. Cl.
*A01H 5/12* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
See application file for complete search history.

*Primary Examiner* — Anne Marie Grunberg
(74) *Attorney, Agent, or Firm* — Penny J. Aguirre

(57) ABSTRACT

A new cultivar of *Sedum* plant named 'Dream Dazzler' that is characterized by its very compact plant habit with stems that do not flop, its plant size that reaches about 23 cm (9 inches) in height and 46 cm (18 inches) in spread, its unique variegated foliage colors; under full sun exposure leaves are dark purple with hot pink margins, under part sun exposure leaves are light purple with hot pink margins, under shade conditions leaves are blue-green with white and pink margins, and its resistance to *Sedum* foliage blight and powdery mildew.

2 Drawing Sheets

Botanical classification: *Sedum* hybrid.
Variety denomination: 'Dream Dazzler'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to publications on www.greatgardenplants.com, www.growingcolors.com, www.facebook.com/2Plant/posts/sedum-dream-dazzler, www.2plant.com, www.gardencentermag.com, and press releases related to Pack Trials 2018.

BACKGROUND OF THE INVENTION

The present invention relates to a new and distinct cultivar of *Sedum* plant, botanically of hybrid origin and known as *Sedum* 'Dream Dazzler' referred to hereinafter by its cultivar name, 'Dream Dazzler'. The new cultivar of *Sedum* is a hardy herbaceous perennial grown for use as a landscape and container plant and as a groundcover.

'Dream Dazzler' was discovered in August of 2014 by the Inventor outdoors in a container block in Hudsonville, Mich. as a branch sport mutation of *Sedum* 'Plum Dazzled' (U.S. Plant Pat. No. 30,348).

Asexual propagation of the new cultivar was first accomplished by stem tip cuttings in April of 2015 in Hudsonville, Mich. Propagation by tip stem cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Dream Dazzler' as a unique cultivar of *Sedum*.

1. 'Dream Dazzler' exhibits a very compact plant habit with stems that do not flop.
2. 'Dream Dazzler' reaches about 23 cm (9 inches) in height and 46 cm (18 inches) in spread (unique for a variegated *Sedum*).
3. 'Dream Dazzler' exhibits unique variegated foliage colors; under full sun exposure leaves are dark purple with hot pink margins, under part sun exposure leaves are light purple with hot pink margins, under shade conditions leaves are blue-green with white and pink margins.
4. 'Dream Dazzler' has been observed to be resistant to *Sedum* foliage blight and powdery mildew.

The parent plant of 'Dream Dazzler', 'Plum Dazzled', differs from 'Dream Dazzler' in having foliage that is not variegated and solid purple in color. 'Dream Dazzler' can also be most closely compared to the cultivars 'Lajos' (U.S. Plant Pat. No. 14,421) and 'Razzleberry' (U.S. Plant Pat. No. 22,457). 'Lajos' is similar to 'Dream Dazzler' in having variegated foliage and a flowering period in late summer. 'Lajos' differs from 'Dream Dazzler' in having foliage colors with green centers and creamy-white margins, leaves that are twice as larger in size, a taller plant height and fewer stems. 'Razzleberry' is similar to 'Dream Dazzler' in being a ground-cover type *Sedum* and in having similar flower characteristics. 'Razzleberry' differs from 'Dream Dazzler' in having leaves that are non-variegated and light purple in coloration, an earlier blooming period (2 to 3 weeks earlier) and leaves that are slightly larger in size.

BRIEF DESCRIPTION OF THE DRAWINGS

The accompanying colored photographs illustrate the overall appearance and distinct characteristics of the new *Sedum*. The photographs were taken of plants about 9 months in age as grown outdoors in 1-gallon containers in Hudsonville, Mich.

The photograph in FIG. 1 provides a side view of 'Dream Dazzler'.

Figure 1:
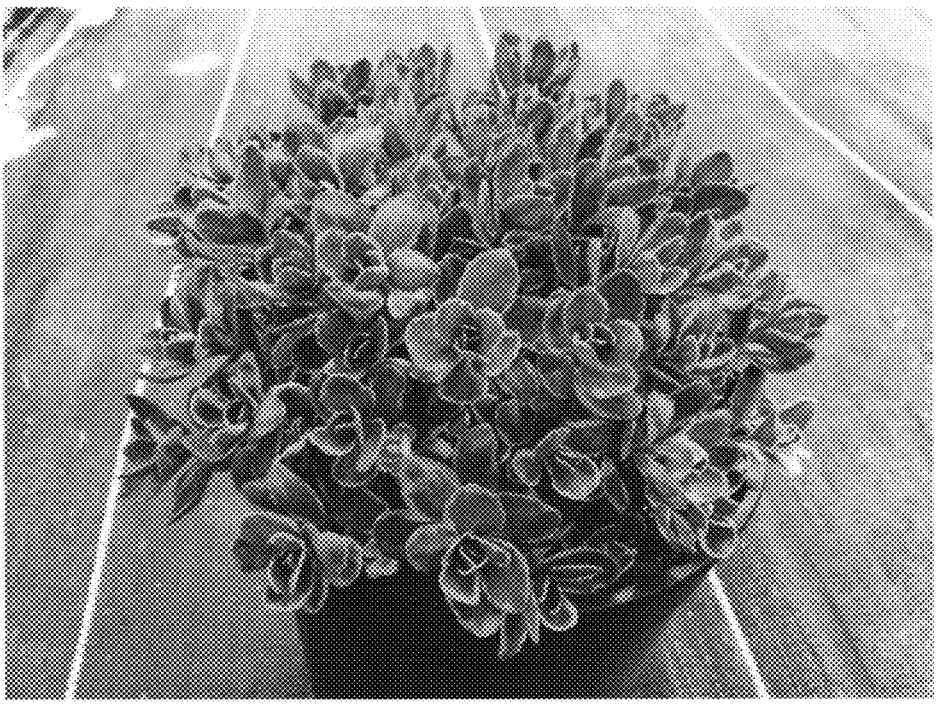
Figure 2:
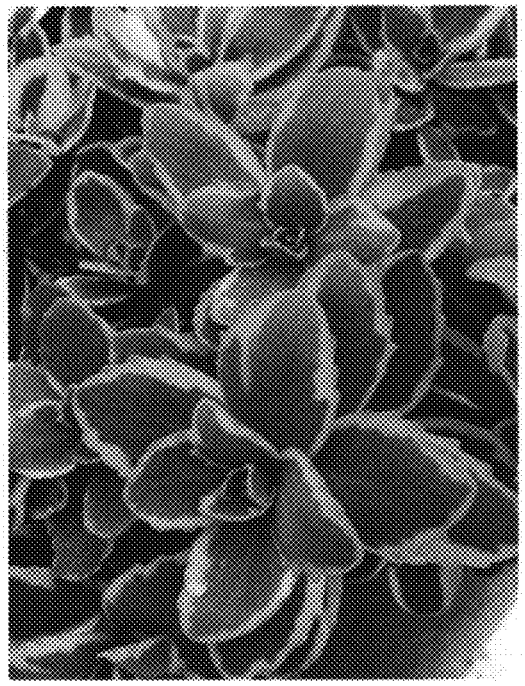

The photograph in FIG. 2 provides a close-up view of the foliage of 'Dream Dazzler'.

Figure 3:
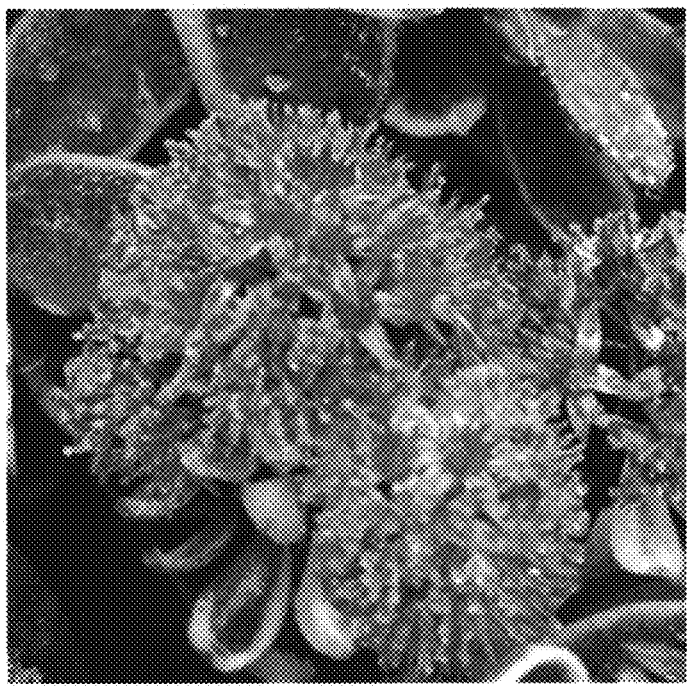

The photograph in FIG. 3 provides a close-up view of the inflorescences of 'Dream Dazzler'.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 6-month-old plants of 'Dream Dazzler' as grown outdoors in 2-qt containers in Hudsonville, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—5 weeks in late summer in Michigan.

*Plant type.*—Herbaceous perennial.

*Plant habit.*—Very compact plant habit, spreading, stems that do not flop.

*Height and spread.*—Reaches about 23 cm (9 inches) in height and 46 cm (18 inches) in spread in the landscape.

*Hardiness.*—At least hardy in U.S.D.A. Zones 4 to 9.

*Diseases and pests.*—Highly resistant to *Sedum* foliage blight (caused by *Septoria sedi*) and powdery mildew (caused by *Erysiphe cichoracearum*), no occurrence of either has been observed during 3 years of observation, no resistance or susceptibility has been observed to pests.

*Root description.*—Fibrous, 159C in color.

*Propagation.*—Stem tip cuttings and division.

*Root development.*—Roots initiate in 15 days and a young plant is fully rooted in a 4-inch container in about 90 days.

*Growth rate.*—Vigorous.

Stem description:

*Stem shape.*—Oval.

*Stem size.*—An average of 26 cm in length (excluding inflorescence), 5 mm in width.

*Internode length.*—Average of 2 cm.

*Stem color.*—Young branches; 145A, heavily to moderately flushed with 182A, mature branches; 138B, heavily flushed with 183A.

*Stem surface.*—Glabrous and shiny.

*Branching habit.*—An average of 21 branches per plant growing from base.

Foliage description:

*Leaf shape.*—Elliptical.

*Leaf division.*—Simple.

*Leaf arrangement.*—Both opposite and alternate.

*Leaf base.*—Acute.

*Leaf apex.*—Acute to bluntly acute.

*Leaf venation.*—Not conspicuous.

*Leaf margins.*—Entire and moderately serrulate.

*Leaf attachment.*—Most leaves are Petiolate, some are sessile.

*Leaf number.*—An average of 34 leaves per branch.

*Leaf orientation.*—Nearly horizontal to slightly upward, slightly cupped.

*Leaf texture.*—Thick, succulent.

*Leaf surface.*—Both surfaces dull and glaucous.

*Leaf color.*—Variegated, upper and lower surface; base to mid-section 137A, mid to upper section N79A and heavily flushed with 63A, margins NN155C and heavily suffused with N66A.

*Leaf size.*—Average of 4 cm in length and 2 cm in width.

Flower description:

*Inflorescence type.*—Dense, slightly rounded cymes with an average of 3 terminal forked branches at terminus and upper lateral nodes, blooms are present on top of the plant.

*Inflorescence size.*—An average of 4 cm in diameter and 5 cm in depth (inclusive of forked branches) per individual cymes and up to 9 cm in length and 6 cm in width for the compound cyme, and up to 17 cm in width and 10 cm in depth for all cymes on a stem.

*Lastingness of inflorescence.*—At least one month.

*Flower type.*—Perfect, spreading, 5-starred.

*Flower number.*—An average of 40 flowers per branched cyme, an average of 10 to 20 flowers per stem.

*Flower fragrance.*—None.

*Flower buds.*—Ovate in shape, about 5 mm length and 2 mm in width, glabrous surface, 63A in color.

*Flower size.*—About 4 mm in depth and 1 cm in diameter.

*Peduncles.*—Round in shape, an average of 1.5 cm in length and 1 mm in width, secondary average 2 mm in length and 0.5 mm in width, 145A, heavily to moderately flushed with 182A, glabrous surface.

*Pedicels.*—Round in shape, an average of 5 mm in length and 0.5 mm in width, 187A in color, glabrous surface.

*Calyx.*—5-parted.

*Sepals.*—5, tube; about 1 mm in length and width, color; N189B, flushed with 187A, lanceolate in shape, entire margin, narrowly acute apex, fused base, glaucous on both surfaces.

*Petals.*—5, spreading, 3 mm in length and 1 mm in width, lanceolate in shape, rounded base, acute apex, entire margin, color; inner surface when opening and fully open; base 65D, rest of surface a blend of 65C, 71A and N74A, outer surface when opening and fully open; base 65D, rest of surface a blend of 65C, N74A and 71A, glabrous on both surfaces.

Reproductive organs:

*Pistils.*—5, showy, held erect, about 3 mm in length 1 mm in width, stigma; minute, smaller than 0.5 mm and 161A in color, style; ovate, rounded in shape, cone like, and 63A in color, ovary; small, single celled and translucent in color.

*Stamens.*—10, about 4 mm in length, filament; very fine, 63A in color, anther; club shaped, about 0.5 mm in length and width, 161A in color, pollen is moderate in quantity and N74A in color.

*Fruit.*—Fruit and seed production has not been observed to date.

It is claimed:

1. A new and distinct variety of *Sedum* plant named 'Dream Dazzler' as described and illustrated herein.

* * * * *